United States Patent
Cauthen, III (10) Patent No.: US 7,670,380 B2
(45) Date of Patent: Mar. 2, 2010

(54) INTERVERTEBRAL DISC ANNULUS STENT

(75) Inventor: Joseph C. Cauthen, III, Gainesville, FL (US)

(73) Assignee: Anulex Technologies, Inc., Minnetonka, MN (US)

( * ) Notice: Subject to any disclaimer, the term of this patent is extended or adjusted under 35 U.S.C. 154(b) by 0 days.

(21) Appl. No.: 11/521,473

(22) Filed: Sep. 15, 2006

(65) Prior Publication Data

US 2007/0061012 A1   Mar. 15, 2007

Related U.S. Application Data

(63) Continuation of application No. 10/985,735, filed on Nov. 10, 2004, which is a continuation of application No. 10/085,040, filed on Mar. 1, 2002, which is a continuation of application No. 09/947,078, filed on Sep. 5, 2001, now Pat. No. 6,592,625, which is a continuation of application No. 09/484,706, filed on Jan. 18, 2000, now abandoned.

(60) Provisional application No. 60/160,710, filed on Oct. 20, 1999.

(51) Int. Cl.
 *A61F 2/44* (2006.01)
(52) U.S. Cl. .............. 623/17.16; 606/249; 606/151; 606/216; 623/902
(58) Field of Classification Search ... 623/17.11–17.16, 623/902
See application file for complete search history.

(56) References Cited

U.S. PATENT DOCUMENTS

| | | | |
|---|---|---|---|
| 4,520,821 A | 6/1985 | Schmidt | |
| 5,152,303 A * | 10/1992 | Allen | 128/898 |
| 5,207,695 A | 5/1993 | Trout | |
| 5,350,399 A | 9/1994 | Erlebacher | |
| 5,397,991 A | 3/1995 | Rogers | |
| 5,411,520 A | 5/1995 | Nash et al. | |
| 5,861,004 A | 1/1999 | Kensey | |
| 5,888,222 A | 3/1999 | Coates | |
| 6,132,465 A * | 10/2000 | Ray et al. | 623/17.16 |

(Continued)

FOREIGN PATENT DOCUMENTS

DE   4323595 C   7/1994

(Continued)

OTHER PUBLICATIONS

International Search Report for PCT/US06/16292 (PCT counterpart of related application) dated Apr. 28, 2006, Blaine R. Copenheaver.

(Continued)

*Primary Examiner*—David Isabella
*Assistant Examiner*—Suba Ganesan
(74) *Attorney, Agent, or Firm*—Faegre & Benson LLP (57) ABSTRACT

A stent, or device for repair and reconstruction of the spinal disc wall, or annulus fibrosus, after surgical incision or pathologic rupture, which is inserted through an aperture into the subannular space. The stent has radial extensions which are caused or allowed to expand into an expanded configuration to bridge the aperture. The stent thereby occludes the defective region from the inside of the vertebral disc and prevents the migration of nucleus pulposus therethrough, while also providing a scaffold for tissue growth.

14 Claims, 9 Drawing Sheets

U.S. PATENT DOCUMENTS

| | | | |
|---|---|---|---|
| 6,183,515 B1 * | 2/2001 | Barlow et al. | 623/16.11 |
| 6,245,107 B1 * | 6/2001 | Ferree | 623/17.16 |
| 6,261,296 B1 * | 7/2001 | Aebi et al. | 606/90 |
| 6,464,712 B1 | 10/2002 | Epstein | |
| 6,506,204 B2 | 1/2003 | Mazzocchi | |
| 6,696,073 B2 | 2/2004 | Boyce | |
| 6,726,696 B1 | 4/2004 | Houser | |
| 6,783,546 B2 | 8/2004 | Zucherman | |
| 6,805,695 B2 | 10/2004 | Keith | |
| 7,033,393 B2 | 4/2006 | Gainor | |
| 7,128,073 B1 | 10/2006 | Van Der Burg | |
| 2002/0077701 A1 | 6/2002 | Kuslich | |
| 2002/0082698 A1 | 6/2002 | Parenteau | |
| 2002/0147461 A1 | 10/2002 | Aldrich | |
| 2003/0040796 A1 | 2/2003 | Ferree | |
| 2003/0074075 A1 | 4/2003 | Thomas | |
| 2003/0195514 A1 | 10/2003 | Trieu | |
| 2004/0039392 A1 | 2/2004 | Trieu | |
| 2004/0054414 A1 | 3/2004 | Trieu | |
| 2004/0092969 A1 | 5/2004 | Kumar | |
| 2004/0097980 A1 | 5/2004 | Ferree | |
| 2004/0138703 A1 | 7/2004 | Alleyne | |
| 2004/0210310 A1 | 10/2004 | Trieu | |
| 2004/0260397 A1 | 12/2004 | Lambrecht et al. | |
| 2005/0033440 A1 | 2/2005 | Lambrecht et al. | |
| 2005/0038519 A1 | 2/2005 | Lambrecht et al. | |
| 2005/0060038 A1 | 3/2005 | Lambrecht et al. | |
| 2006/0060038 A1 | 3/2006 | Cauthen | |
| 2006/0129156 A1 | 6/2006 | Cauthen | |
| 2006/0167553 A1 | 7/2006 | Cauthen | |
| 2006/0173545 A1 | 8/2006 | Cauthen | |
| 2006/0195193 A1 | 8/2006 | Bloemer | |
| 2006/0247776 A1 | 11/2006 | Kim | |
| 2006/0282167 A1 | 12/2006 | Lambrecht | |
| 2007/0067040 A1 | 3/2007 | Ferree | |
| 2007/0100349 A1 | 5/2007 | O'Neil | |

FOREIGN PATENT DOCUMENTS

| | | |
|---|---|---|
| EP | 0 020 021 A2 | 12/1980 |
| EP | 0 025 706 A1 | 3/1981 |
| EP | 0 042 953 A2 | 1/1982 |
| EP | 0 049 978 A1 | 4/1982 |
| EP | 0 061 037 A1 | 9/1982 |
| EP | 0 062 832 A1 | 10/1982 |
| EP | 0 076 409 A1 | 4/1983 |
| EP | 0 110 316 A2 | 6/1984 |
| EP | 0 112 107 A2 | 6/1984 |
| EP | 0 121 246 A2 | 10/1984 |
| EP | 0 122 902 A2 | 10/1984 |
| EP | 0 126 570 A2 | 11/1984 |
| EP | 0 145 577 A2 | 6/1985 |
| EP | 0 193 784 A2 | 9/1986 |
| EP | 0 195 818 A1 | 10/1986 |
| GB | 2054383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 8/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |

OTHER PUBLICATIONS

Ahlgren, B.D., MD., et al., "Anular Incision Technique on the Strength and Multidirectional Flexibility of the Healing Intervertebral Disc," Spine 19(8):948-954 (1994).

Ahlgren, B.D., MD., et al., "Effect of Anular Repair on the Healing Strength of the Intervertebral Disc," Spine 25(17):2165-2170 (2000).

Cauthen, Joseph, Draft Abstract entitled "Microsurgical Annular Reconstruction (Annuloplasty) Following Lumbar Microdiscectomy: Preliminary Report of a New Technique" from abstracts@neurosurgery.org. Sep. 4, 1998.

Cauthen, Joseph C., MD., "Microsurgical Annular Reconstruction (Annuloplasty) Following Lumbar Microdiscectomy: Preliminary Report of a New Technique," Abstract for Poster Presentation, AANS/CNS Section On Disorders Of The Spine And Peripheral Nerves Annual Meeting (1999).

Lehmann, Thomas R., M.D., et al., "Refinements in Technique For Open Lumbar Discectomy," International Society for the Study of the Lumbar Spine (1997).

Mineiro, J., et al., "Dynamic Neutralization With Dynesys Review of 113 Cases with More than 1 Year Follow-Up," Spineweek 2004, Porto, Portugal May 30th to Jun. 5th, 2004, Abstract B19, p. 181.

Ordway, N.R., et al., "Failure Properties of a Hydrogel Nucleus in the Intervertebral Disc," North American Spine Society, pp. 168-169 (1997).

Osti, O.L., et al., "Annular Tears and Disc Degeneration in the Lumbar Spine," The Journal of Bone and Joint Surgery 74-B(5):678-82 (1992).

Panjabi, Manohar, PhD., et al., "Intrinsic Disc Pressure as a Measure of Integrity of the Lumbar Spine," Spine 13(8):913-17 (1988).

Ray, Charles D., "Prosthetic Disc Nucleus Implants: Update," North American Spine Society 13th Annual Meeting, p. 252.

Yasargil, M.G., "Microsurgical Operation of Hemiated Lumbar Disc," Lumbar Disc Adult Hydrocephalus, p. 81 (1977).

Copending U.S. Appl. No. 10/075,615, filed Feb. 15, 2002 by Cauthen.

Copending U.S. Appl. No. 10/085,040, filed Mar. 1, 2002 by Cauthen.

Copending U.S. Appl. No. 10/352,981, filed Jan. 29, 2003 by Cauthen.

Copending U.S. Appl. No. 10/394,061, filed Mar. 24, 2003 by Cauthen.

Copending U.S. Appl. No. 10/394,266, filed Mar. 24, 2003 by Cauthen.

Copending U.S. Appl. No. 10/394,008, filed Mar. 24, 2003 by Cauthen.

Copending U.S. Appl. No. 10/392,733, filed Mar. 19, 2003 by Cauthen.

Copending U.S. Appl. No. 10/985,735, filed Nov. 10, 2004 by Cauthen.

Copending U.S. Appl. No. 11/120,750, filed May 3, 2005 by Cauthen et al.

Copending U.S. Appl. No. 11/235,764, filed Sep. 26, 2005 by Wales.

Copending U.S. Appl. No. 11/386,642, filed Mar. 23, 2006 by Cauthen et al.
Copending U.S. Appl. No. 11/398,583, filed Apr. 6, 2006 by Cauthen.
Copending U.S. Appl. No. 11/410,420, filed Apr. 25, 2006 by Cauthen.
Copending U.S. Appl. No. 11/313,738, filed Dec. 22, 2005 by Cauthen.
Copending U.S. Appl. No. 11/351,657, filed Feb. 10, 2006 by Cauthen.
Copending U.S. Appl. No. 11/355,426, filed Feb. 16, 2006 by Cauthen.
Copending U.S. Appl. No. 11/376,301, filed Mar. 16, 2006 by Cauthen.
Copending U.S. Appl. No. 11/350,843, filed Feb. 10, 2006 by Cauthen et al.
Copending U.S. Appl. No. 11/386,616, filed Mar. 23, 2006 by Cauthen et al.
Copending U.S. Appl. No. 11/512,251, filed Aug. 30, 2006 by Cauthen et al.
Copending U.S. Appl. No. 11/558,034, filed Nov. 9, 2006 by Cauthen.
Copending U.S. Appl. No. 11/841,513, filed Aug. 20, 2007 by Cauthen.
Copending U.S. Appl. No. 11/556,878, filed Nov. 6, 2006 by Cauthen et al.
Copending U.S. Appl. No. 11/557,997, filed Nov. 9, 2006 by Cauthen et al.
Copending U.S. Appl. No. 11/559,457, filed Nov. 14, 2006 by Cauthen et al.
Copending U.S. Appl. No. 11/608,480, filed Dec. 8, 2006 by Cauthen et al.
Copending U.S. Appl. No. 11/622,631, filed Jan. 12, 2007 by Cauthen et al.
Copending U.S. Appl. No. 11/686,599, filed Mar. 15, 2007 by Cauthen et al.
Copending U.S. Appl. No. 11/527,903, filed Sep. 26, 2006 by Cauthen et al.

* cited by examiner

FIG. 12B

INTERVERTEBRAL DISC ANNULUS STENT

CROSS-REFERENCE TO RELATED APPLICATIONS

This application is a continuation of U.S. patent application Ser. No. 10/985,735, filed Nov. 10, 2004, which is a continuation of U.S. patent application Ser. No. 10/085,040, filed Mar. 1, 2002, which is a continuation of U.S. patent application Ser. No. 09/947,078, filed Sep. 5, 2001, now U.S. Pat. No. 6,592,625 which is a continuation of U.S. patent application Ser. No. 09/484,706, filed Jan. 18, 2000, now abandoned which claims the benefit of U.S. Provisional Application No. 60/160,710, filed Oct. 20, 1999. The entire contents of each of the above are incorporated herein by reference.

FIELD OF THE INVENTION

The invention generally relates to a surgical method of intervertebral disc wall reconstruction. The invention also relates to an annular repair device, or stent, for annular disc repair. The effects of said reconstruction are restoration of disc wall integrity and reduction of the failure rate (3-21%) of a common surgical procedure (disc fragment removal or discectomy). This surgical procedure is performed about 390,000 times annually in the United States.

BACKGROUND OF THE INVENTION

The spinal column is formed from a number of vertebrae, which in their normal state are separated from each other by cartilaginous intervertebral discs. The intervertebral disc acts in the spine as a crucial stabilizer, and as a mechanism for force distribution between the vertebral bodies. Without the disc, collapse of the intervertebral space occurs in conjunction with abnormal joint mechanics and premature development of arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of loose tissue, having about 85% water content, which moves about during bending from front to back and from side to side.

The aging process contributes to gradual changes in the intervertebral discs. The annulus loses much of its flexibility and resilience, becoming more dense and solid in composition. The aging annulus is also marked by the appearance on propagation of cracks or fissures in the annular wall. Similarly, the nucleus dessicates, increasing viscosity and thus losing its fluidity. In combination, these features of the aged intervertebral discs result in less dynamic stress distribution because of the more viscous nucleus pulposus, and less ability to withstand localized stresses by the annulus fibrosus due to its dessication, loss of flexibility and the presence of fissures. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

The surgical standard of care for treatment of herniated, displaced or ruptured intervertebral discs is fragment removal and nerve decompression without a requirement to reconstruct the annular wall. While results are currently acceptable, they are not optimal. Various authors report 3.1-21% recurrent disc herniation, representing a failure of the primary procedure and requiring re-operation for the same condition. An estimated 10% recurrence rate results in 39,000 re-operations in the United States each year.

An additional method of relieving the symptoms is thermal annuloplasty, involving the heating of sub-annular zones in the non-herniated painful disc, seeking pain relief, but making no claim of reconstruction of the ruptured, discontinuous annulus wall.

There is currently no known method of annulus reconstruction, either primarily or augmented with an annulus stent.

BRIEF SUMMARY OF THE INVENTION

The present invention provides methods and related materials for reconstruction of the disc wall in cases of displaced, herniated, ruptured, or otherwise damaged intervertebral discs. In accordance with the invention, an annulus stent is disclosed for repair of an intervertebral disc annulus, comprising a centralized hub section, said hub section comprising lateral extensions from the hub section.

In an exemplary embodiment, one or more mild biodegradable surgical sutures are placed at about equal distances along the sides of a pathologic aperture in the ruptured disc wall (annulus) or along the sides of a surgical incision in the annular wall, which may be weakened or thinned.

Sutures are then tied in such fashion as to draw together the sides of the aperture, effecting reapproximation or closure of the opening, to enhance natural healing and subsequent reconstruction by natural tissue (fibroblasts) crossing the now surgically narrowed gap in the disc annulus.

A 25-30% reduction in the rate of recurrence of disc nucleus herniation through this aperture, has been achieved using this method.

In another embodiment, the method can be augmented by creating a subannular barrier in and across the aperture by placement of a patch of human muscle fascia (the membrane covering the muscle) or any other autograft, allograft, or xenograft acting as a bridge or a scaffold, providing a platform for traverse of fibroblasts or other normal cells of repair existing in and around the various layers of the disc annulus, prior to closure of the aperture.

A 30-50% reduction in the rate of recurrence of disc herniation has been achieved using the aforementioned fascial augmentation with this embodiment.

Having demonstrated that human muscle fascia is adaptable for annular reconstruction, other biocompatible membranes can be employed as a bridge, stent, patch or barrier to subsequent migration of the disc nucleus through the aperture. Such biocompatible materials may be, for example, medical grade biocompatible fabrics, biodegradable polymeric sheets, or form fitting or non-form fitting fillers for the cavity created by removal of a portion of the disc nucleus pulposus in the course of the disc fragment removal or discectomy. The prosthetic material can be placed in and around the intervertebral space, created by removal of the degenerated disc fragments.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

DETAILED DESCRIPTION OF THE INVENTION

Reference will now be made in detail to an illustrative embodiment of the invention, which appears in the accompanying drawings. Wherever possible, the same reference numbers will be used throughout the drawings to refer to the same or like parts.

Figure 7:
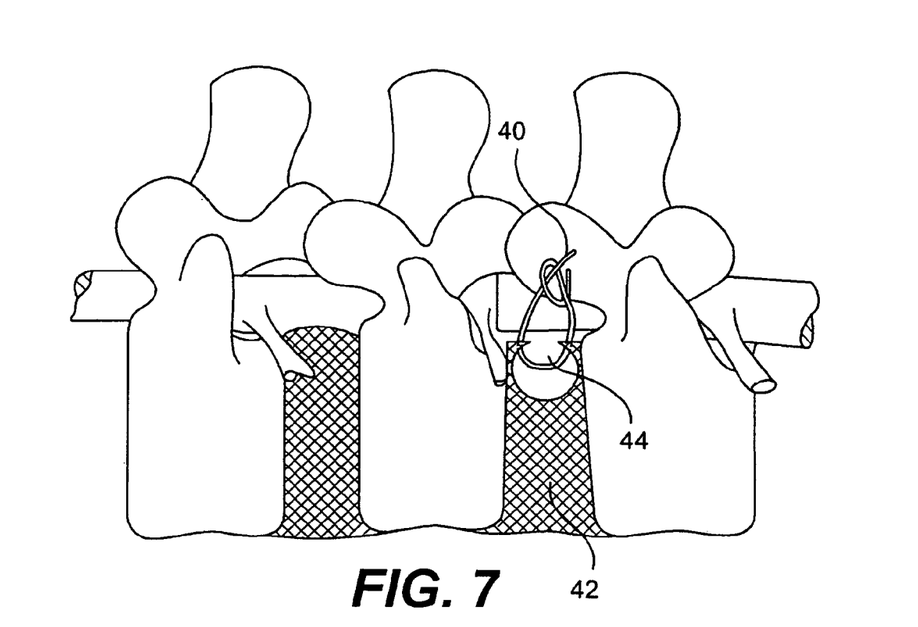
FIG. 7 shows a primary closure of an opening in the disc annulus.

In one embodiment of the present invention, as shown in FIG. 7, a damaged annulus 42 is repaired by use of surgical sutures 40. One or more surgical sutures 40 are placed at about equal distances along the sides of a pathologic aperture 44 in the annulus 42. Reapproximation or closure of the aperture 44 is accomplished by tying the sutures 40 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 40 are biodegradable, but permanent non-biodegradable may be utilized.

Additionally, to repair a weakened or thinned wall of a disc annulus 42, a surgical incision is made along the weakened or thinned region of the annulus 42 and one or more surgical sutures 40 can be placed at about equal distances laterally from the incision. Reapproximation or closure of the incision is accomplished by tying the sutures 40 so that the sides of the incision are drawn together. The reapproximation or closure of the incision enhances the natural healing and subsequent reconstruction by the natural tissue crossing the now surgically narrowed gap in the annulus 42. Preferably, the surgical sutures 40 are biodegradable, but permanent non-biodegradable materials may be utilized.

In an alternative embodiment, the method can be augmented by the placement of a patch of human muscle fascia or any other autograft, allograft or xenograft in and across the aperture 44. The patch acts as a bridge in and across the aperture 44, providing a platform for traverse of fibroblasts or other normal cells of repair existing in and around the various layers of the disc annulus 42, prior to closure of the aperture 44.

Figure 8A:
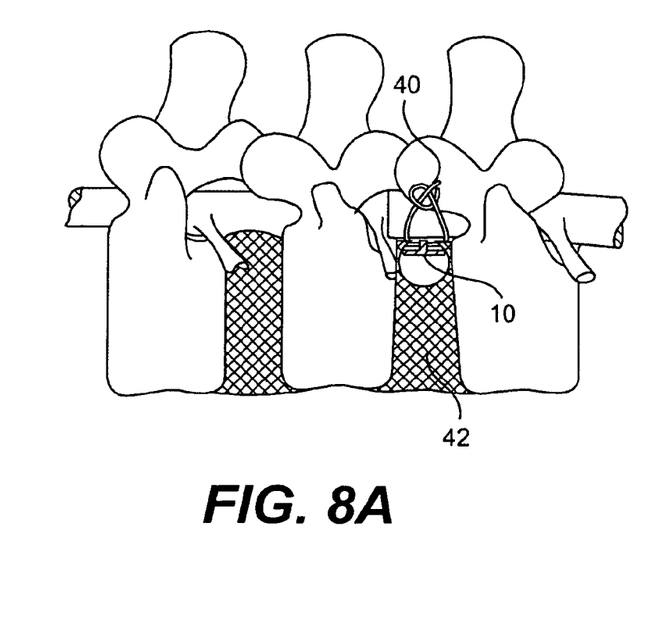
FIGS. 8A-8B show a primary closure with a stent.
Figure 8B:
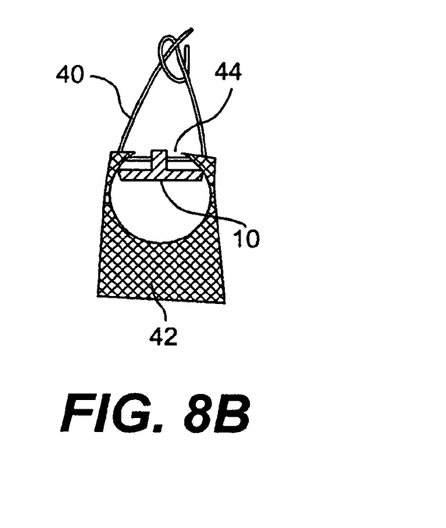

In a further embodiment, as shown in FIGS. 8A-B a biocompatible membrane can be employed as an annulus stent 10, being placed in and across the aperture 44. The annulus stent 10 acts as a bridge in and across the aperture 44, providing a platform for a traverse of fibroblasts or other normal cells of repair existing in and around the various layers of the disc annulus 42, prior to closure of the aperture 44.

Figure 1:
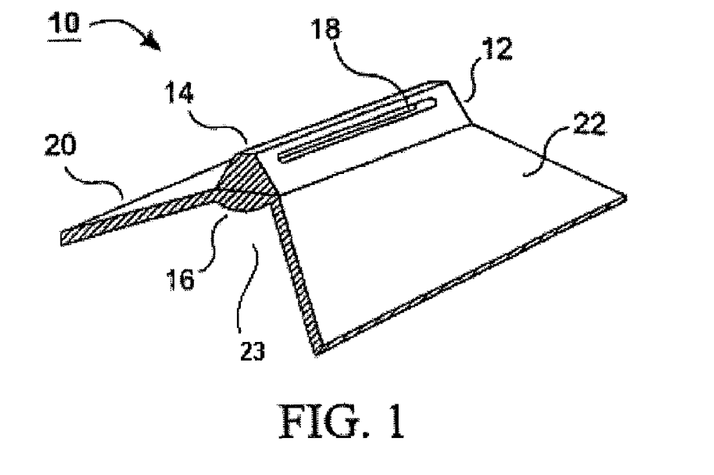
FIG. 1 shows a perspective view of an illustrative embodiment of an annulus stent.
Figure 2:
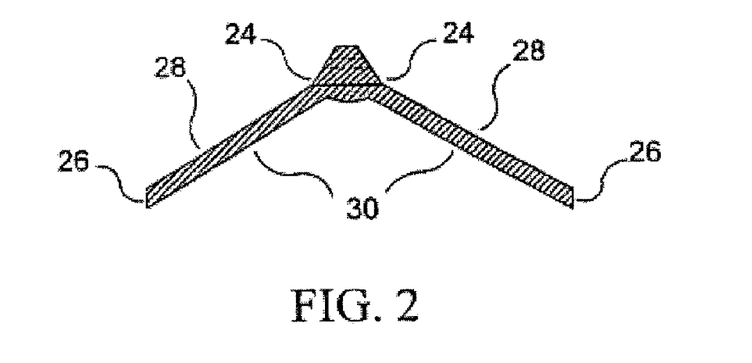
FIG. 2 shows a front view of the annulus stent of FIG. 1.
Figure 3:
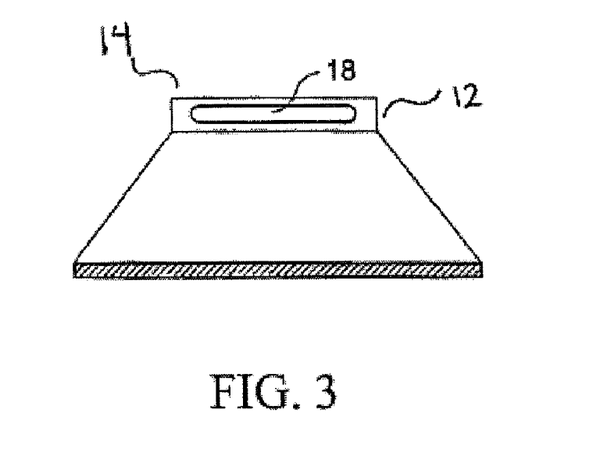
FIG. 3 shows a side view of the annulus stent of FIG. 1.

In an illustrative embodiment, as shown in FIGS. 1-3, the annulus stent 10 comprises a centralized vertical extension 12, with an upper section 14 and a lower section 16. The centralized vertical extension 12 can be trapezoid in shape through the width and may be from about 8 mm-12 mm in length.

Figure 4A:
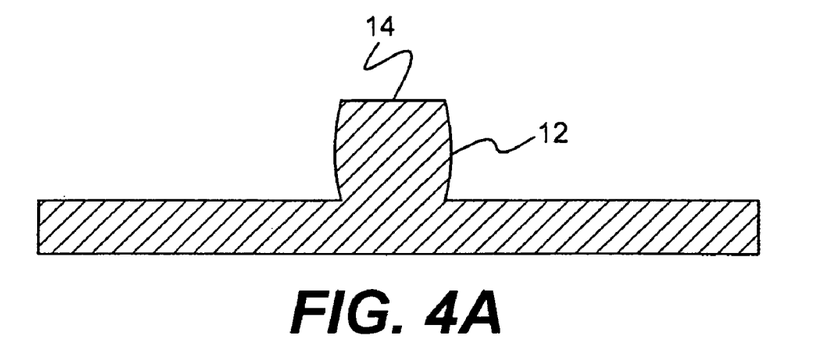
FIGS. 4A-4C show a front view of alternative illustrative embodiments of an annulus stent.
Figure 4B:
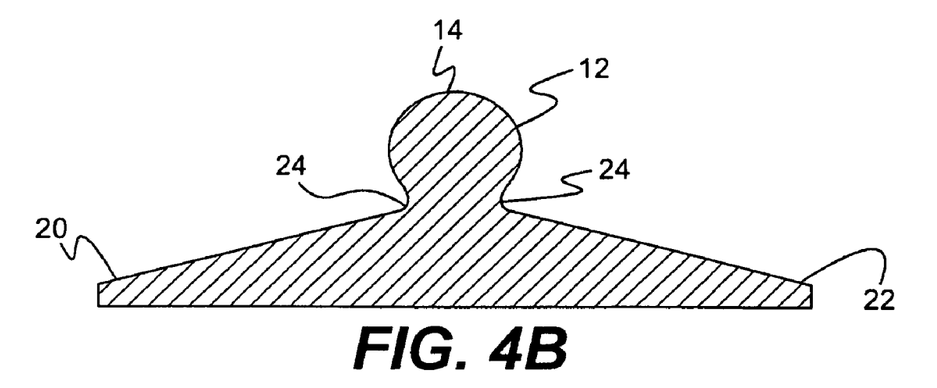
Figure 4C:
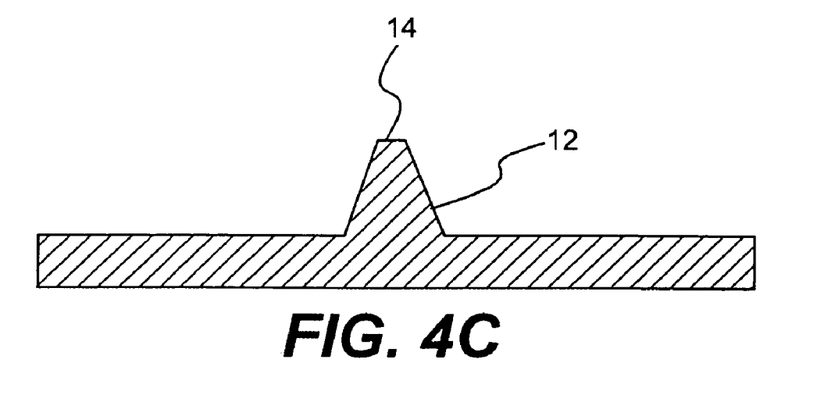

Additionally, the upper section 14 of the centralized vertical extension 12 may be any number of different shapes, as shown in FIGS. 4A and 4B, with the sides of the upper section 14 being curved or with the upper section 14 being circular in shape. Furthermore, the annulus stent 10 may contain a recess between the upper section 14 and the lower section 16, enabling the annulus stent 10 to form a compatible fit with the edges of the aperture 44.

The upper section 14 of the centralized vertical extension 12 can comprise a slot 18, where the slot 18 forms an orifice through the upper section 14. The slot 18 is positioned within the upper section 14 such that it traverses the upper section's 14 longitudinal axis. The slot 18 is of such a size and shape that sutures, tension bands, staples or any other type of fixation device known in the art may be passed through, to affix the annulus stent 10 to the disc annulus 42.

In an alternative embodiment, the upper section 14 of the centralized vertical extension 12 may be perforated. The perforated upper section 14 contains a plurality of holes that traverse the longitudinal axis of upper section 14. The perforations are of such a size and shape that sutures, tension bands, staples or any other type of fixation device known the art may be passed through, to affix the annulus stent 10 to the disc annulus 42.

The lower section 16 of the centralized vertical extension 12 can comprise a pair of lateral extensions, a left lateral extension 20 and a right lateral extension 22. The lateral extensions 20 and 22 comprise an inside edge 24, an outside edge 26, an upper surface 28, and a lower surface 30. The lateral extensions 20 and 22 can have an essentially constant thickness throughout. The inside edge 24 is attached to and is about the same length as the lower section 16. The outside edge 26 can be about 8 mm-16 mm in length. The inside edge 24 and the lower section 16 meet to form a horizontal plane, essentially perpendicular to the centralized vertical extension 12. The upper surface 28 of the lateral extensions 20 and 22 can form an angle from about 0°-60° below the horizontal plane, thereby forming an opening or recess 23 in the annulus stent 10. The width of the annulus stent 10 may be from about 3 mm-5 mm.

Additionally, the upper surface 28 of the lateral extensions 20 and 22 may be barbed for fixation to the inside surface of the disc annulus 42 and to resist expulsion through the aperture 44.

In an alternative embodiment, as shown in FIG. 4B, the lateral extensions 20 and 22 have a greater thickness at the inside edge 24 than at the outside edge 26.

In an illustrative embodiment, the annulus stent 10 is a solid unit, formed from one or more of the flexible resilient biocompatible or bioresorbable materials well know in the art.

For example, the annulus stent 10 may be made from: a porous matrix or mesh of biocompatible and bioresorbable fibers acting as a scaffold to regenerate disc tissue and replace annulus fibrosus as disclosed in, for example, U.S. Pat. No. 5,108,438 (Stone) and U.S. Pat. No. 5,258,043 (Stone), a strong network of inert fibers intermingled with a bioresorbable (or bioabsorbable) material which attracts tissue ingrowth as disclosed in, for example, U.S. Pat. No, 4,904, 260 (Ray et al.); a biodegradable substrate as disclosed in, for example, U.S. Pat. No. 5,964,807 (Gan at al.); or an expandable polytetrafluoroethylene (ePTFE), as used for conventional vascular grafts, such as those sold by W. L. Gore and Associates, Inc. under the trademarks GORE-TEX and PRE-CLUDE, or by Impra, Inc. under the trademark IMPRA.

Furthermore, the annulus stent 10, may contain hygroscopic material for a controlled limited expansion of the annulus stent 10 to fill the evacuated disc space cavity.

Additionally, the annulus stent 10 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

Figure 5A:
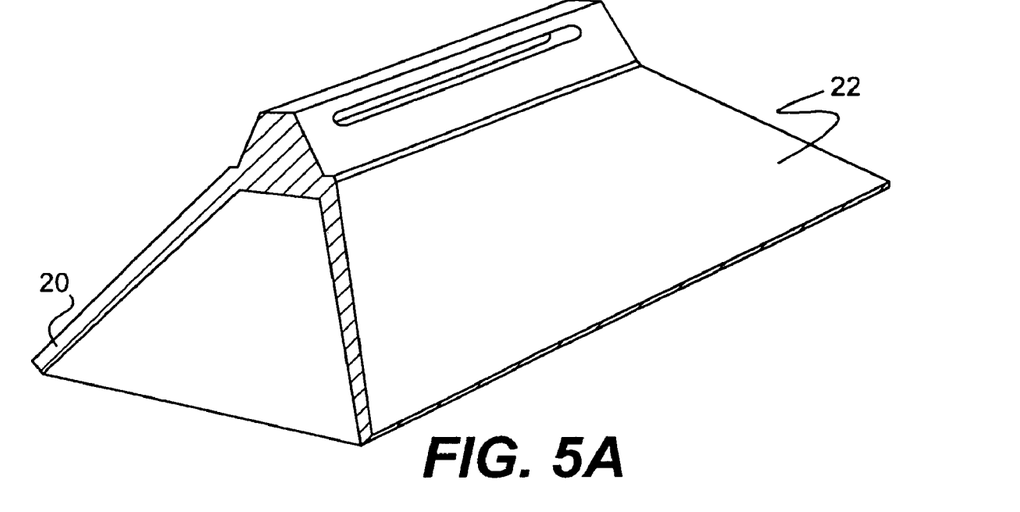
FIGS. 5A-5B show the alternative embodiment of a further illustrative embodiment of an annulus stent.
Figure 5B:
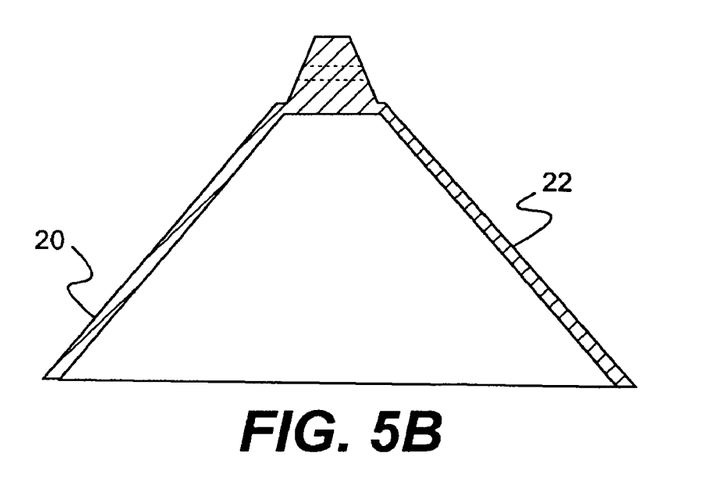
Figure 6A:
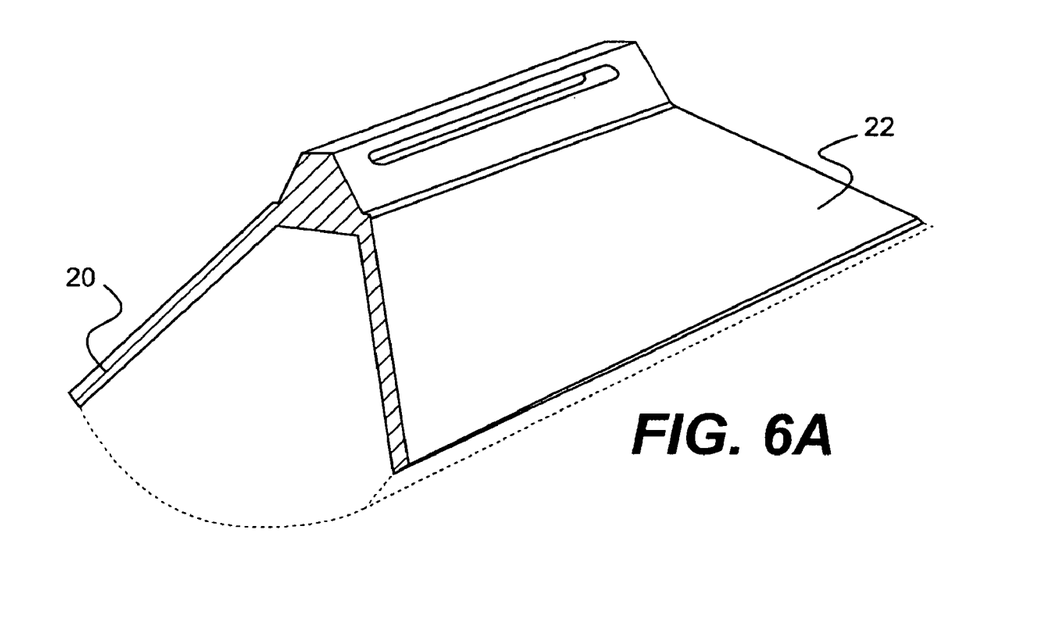
FIGS. 6A-6B show the alternative embodiment of a further illustrative embodiment of an annulus stent.
Figure 6B:
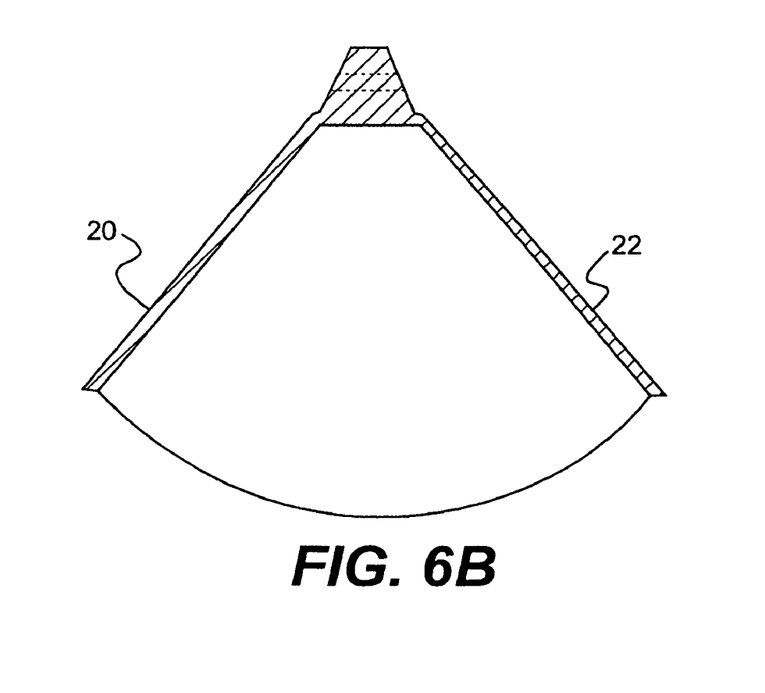

In further embodiments, as shown in FIGS. 5AB-6AB, the left and right lateral extensions 20 and 22 join to form a solid pyramid or cone. Additionally, the left and right lateral extensions 20 and 22 may form a solid trapezoid, wedge, or bullet shape. The solid formation may be a solid biocompatible or bioresorbable flexible material, allowing the lateral extensions 20 and 22 to be compressed for insertion into aperture 44, then to expand conforming to the shape of the annulus' 42 inner wall.

Alternatively, a compressible core may be attached to the lower surface 30 of the lateral extensions 20 and 22, forming a pyramid, cone, trapezoid, wedge, or bullet shape. The compressible core may be made from one of the biocompatible or bioresorbable resilient foams well known in the art. The core can also comprise a fluid-expandable membrane, e.g., a balloon. The compressible core allows the lateral extensions 20 and 22 to be compressed for insertion into aperture 44, then to expand conforming to the shape of the annulus' 42 inner wall and to the cavity created by pathologic extrusion or surgical removal of the disc fragment.

In an illustrative method of use, as shown in FIGS. 11A-D, the lateral extensions 20 and 22 are compressed together for insertion into the aperture 44 of the disc annulus 42. The annulus stent 10 is then inserted into the aperture 44, where the lateral extensions 20, 22 expand. In an expanded configuration, the upper surface 28 can substantially conform to the contour of the inside surface of the disc annulus 42. The upper section 14 is positioned within the aperture 44 so that the annulus stent 10 may be secured to the disc annulus 42, using means well known in the art.

In an alternative method, where the length of the aperture 44 is less than the length of the outside edge 26 of the annulus stent 10, the annulus stent 10 can be inserted laterally into the aperture 44. The lateral extensions 20 and 22 are compressed, and the annulus stent 10 can then be laterally inserted into the aperture 44. The annulus stent 10 can then be rotated inside the disc annulus 42, such that the upper section 14 can be held back through the aperture 44. The lateral extensions 20 and 22 are then allowed to expand, with the upper surface 28 contouring to the inside surface of the disc annulus 42. The upper section 14 can be positioned within, or proximate to, the aperture 44 in the subannular space such that the annulus stent 10 may be secured to the disc annulus, using means well known in the art.

Figure 9:
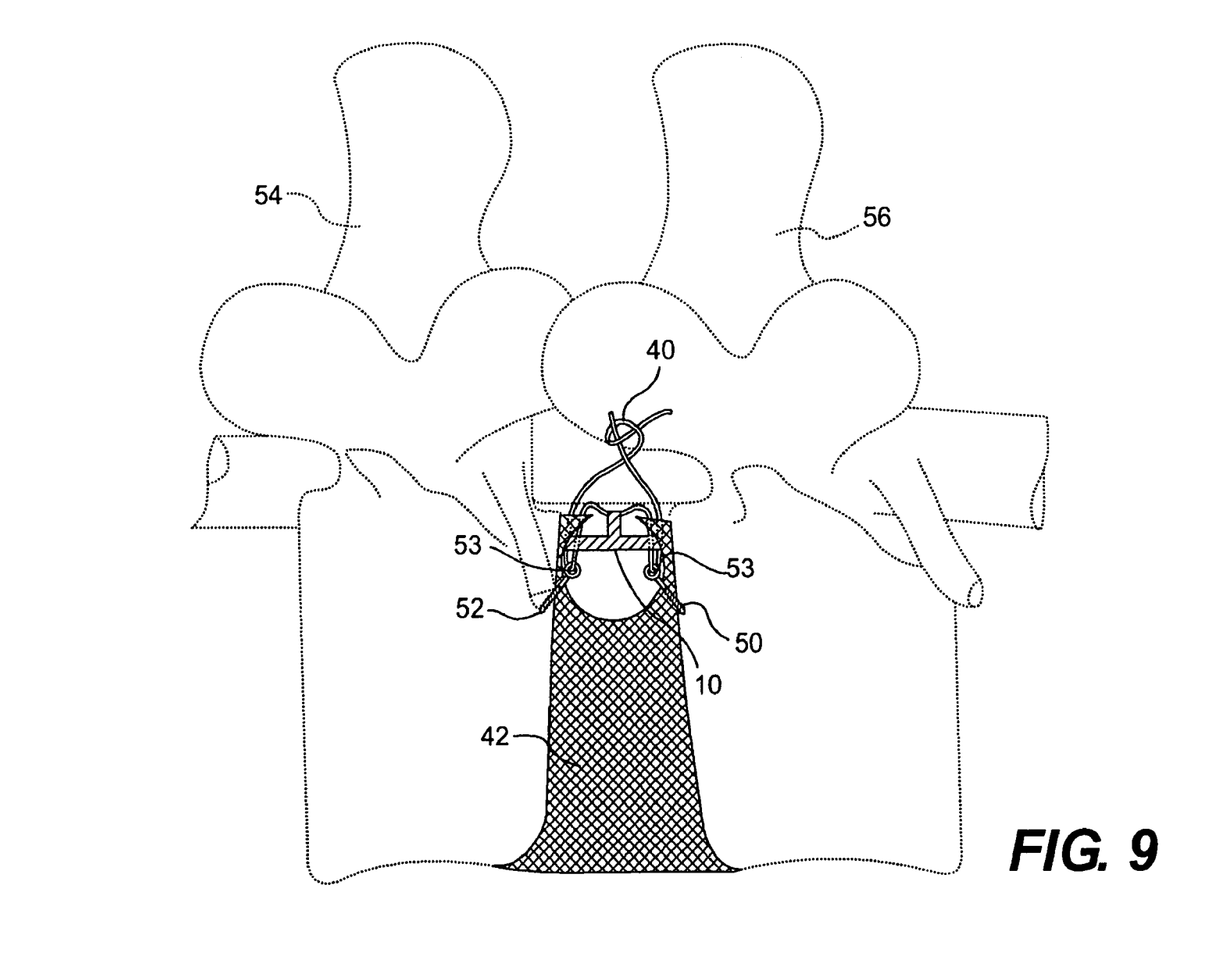
FIG. 9 shows a method of suturing an annulus stent into the disc annulus, utilizing sub-annular fixation points.

In an alternative method of securing the annulus stent 10 in the aperture 44, as shown in FIG. 9, a first surgical screw 50 and second surgical screw 52, with eyeholes 53 located at the top of the screws 50 and 52, are opposingly inserted into the adjacent vertebrae 54 and 56 below the annulus stent 10. After insertion of the annulus stent 10 into the aperture 44, a suture 40 is passed down though the disc annulus 42, adjacent to the aperture 44, through the eye hole 53 on the first screw 50 then back up through the disc annulus 42 and through the orifice 18 on the annulus stent 10. This is repeated for the second screw 52, after which the suture 40 is secured. One or more surgical sutures 40 are placed at about equal distances along the sides of the aperture 44 in the disc annulus 42. Reapproximation or closure of the aperture 44 is accomplished by tying the sutures 40 in such a fashion that the sides of the aperture 44 are drawn together. The reapproximation or closure of the aperture 44 enhances the natural healing and subsequent reconstruction by the natural tissue crossing the now surgically narrowed gap in the annulus 42. Preferably, the surgical sutures 40 are biodegradable but permanent non-biodegradable forms may be utilized. This method should decrease the strain on the disc annulus 42 adjacent to the aperture 44, precluding the tearing of the sutures through the disc annulus 42.

It is anticipated that fibroblasts will engage the fibers of the polymer or fabric of the intervertebral disc stent 10, forming a strong wall duplicating the currently existing condition of healing seen in the normal reparative process.

Figure 10A:
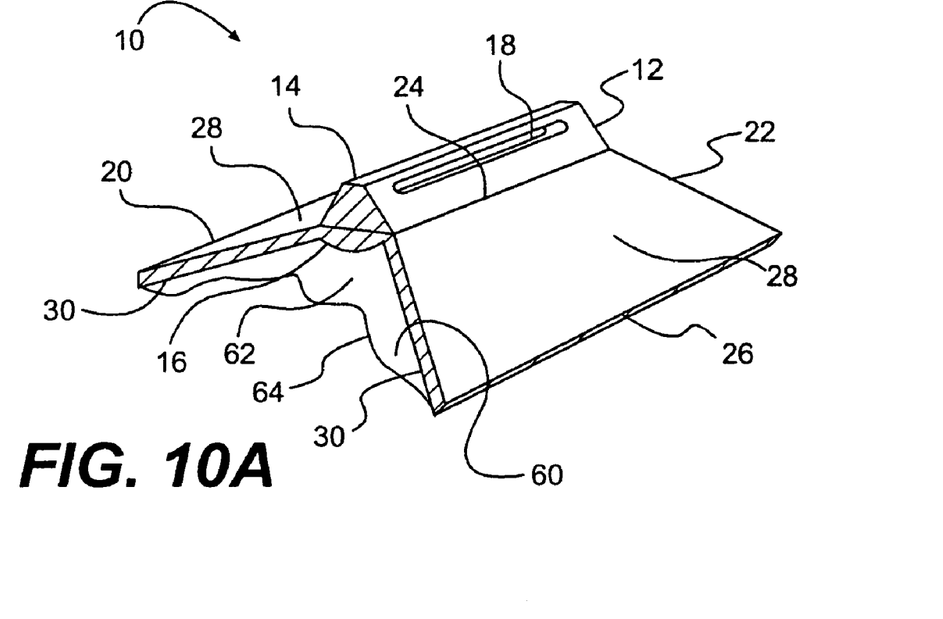
FIGS. 10A-10B show a further illustrative embodiment of an annulus stent with flexible bladder being expanded into the disc annulus.
Figure 10B:
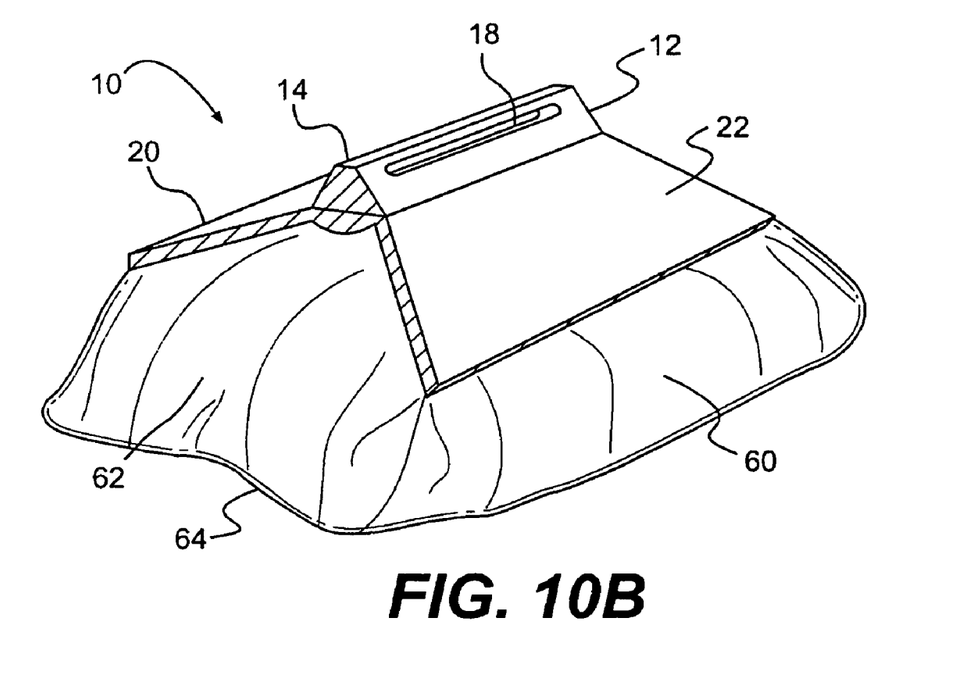
Figure 11A:
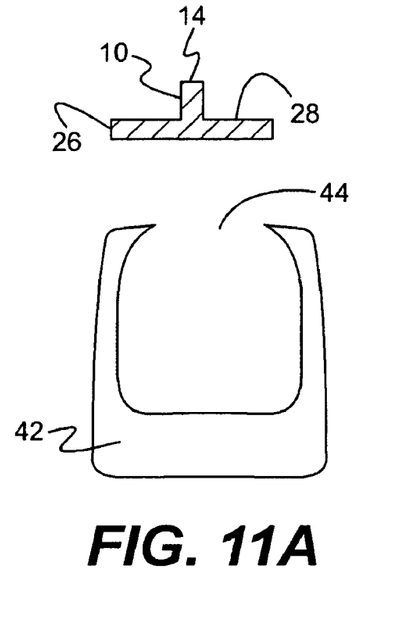
FIGS. 11A-11D show an annulus stent being inserted into the disc annulus.
Figure 11B:
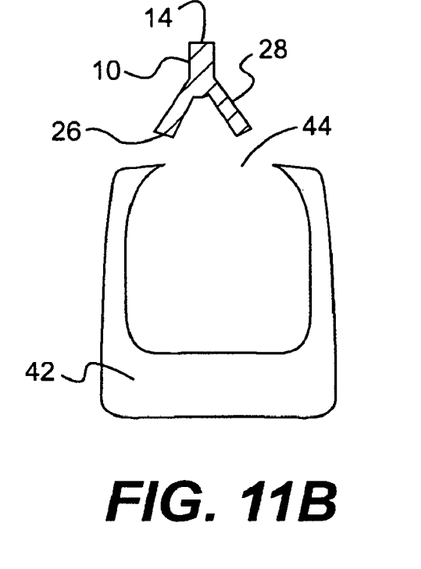
Figure 11C:
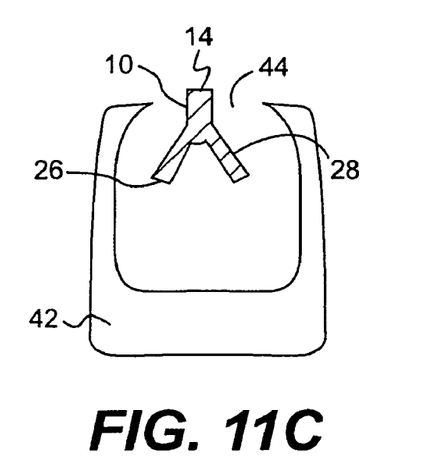
Figure 11D:
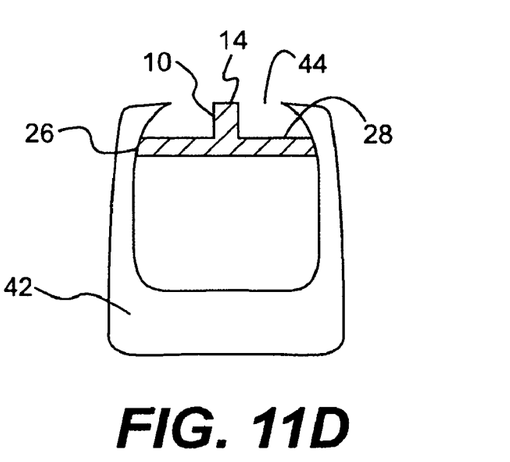

In an additional embodiment, as shown in FIGS. 10A-B, a flexible bladder 60 is attached to the lower surface 30 of the annulus stent 10. The flexible bladder 60 comprises an internal cavity 62 surrounded by a membrane 64, where the membrane 64 is made from a thin flexible biocompatible material. The flexible bladder 60 is attached to the lower surface 30 of the annulus stent 10 in an unexpanded condition. The flexible bladder 60 is expanded by injecting a biocompatible fluid or expansive foam, as known in the art, into the internal cavity 62. The exact size of the flexible bladder 60 can be varied for different individuals. The typical size of an adult nucleus is about 2 cm in the semi-minor axis, 4 cm in the semi-major axis, and 1.2 cm in thickness.

In an alternative embodiment, the membrane 64 is made of a semi-permeable biocompatible material.

In an illustrative embodiment, a hydrogel is injected into the internal cavity 62 of the flexible bladder 60. A hydrogel is a substance formed when an organic polymer (natural or synthetic) is cross-linked via, covalent, ionic, or hydrogen bonds to create a three-dimensional open-lattice structure, which entraps water molecules to form a gel. The hydrogel may be used in either the hydrated or dehydrated form.

Figure 12A:
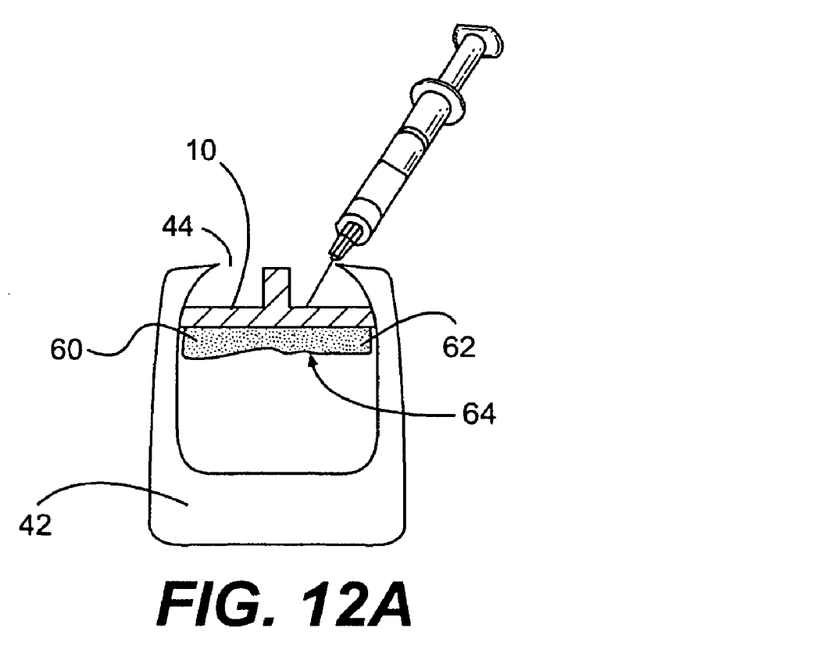
FIGS. 12A-12B show an annulus stent with a flexible bladder being expanded.
Figure 12B:
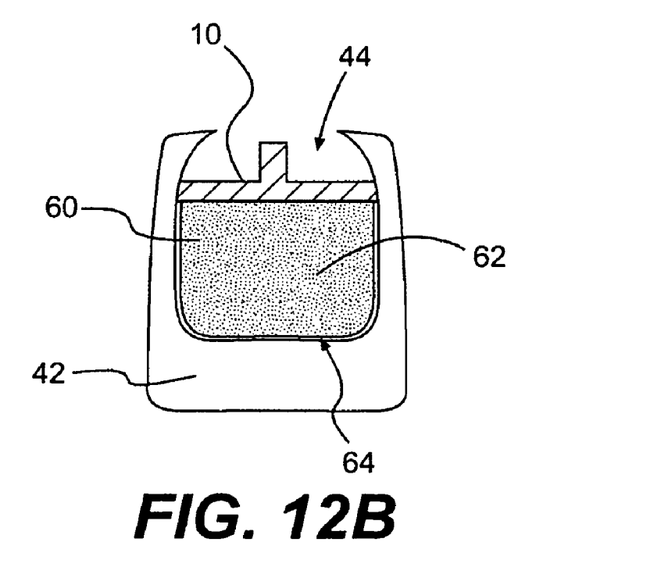

In a method of use, where the annulus stent 10 has been inserted into the aperture 44, as has been previously described and shown in FIGS. 12A-B, an injection instrument, as known in the art, such as a syringe, is used to inject the biocompatible fluid or expansive foam into the internal cavity 62 of the flexible bladder 60. The biocompatible fluid or expansive foam is injected through the annulus stent 10 into the internal cavity 62 of the flexible bladder 60. Sufficient material is injected into the internal cavity 62 to expand the flexible bladder 60 to fill the void in the intervertebral disc cavity. The use of the flexible bladder 60 is particularly useful when it is required to remove all or part of the intervertebral disc nucleus.

The surgical repair of an intervertebral disc may require the removal of the entire disc nucleus, being replaced with an implant, or the removal of a portion of the disc nucleus thereby leaving a void in the intervertebral disc cavity. The flexible bladder 60 allows for the removal of only the damaged section of the disc nucleus, with the expanded flexible bladder 60 filling the resultant void in the intervertebral disc cavity. A major advantage of the annulus stent 10 with the flexible bladder 60 is that the incision area in the annulus 42 can be reduced in size, as there is no need for the insertion of an implant into the intervertebral disc cavity.

In an alternative method of use, a dehydrated hydrogel is injected into the internal cavity 62 of the flexible bladder 60. Fluid, from the disc nucleus, passes through the semipermeable membrane 64 hydrating the dehydrated hydrogel. As the hydrogel absorbs the fluid the flexible bladder 60 expands, filling the void in the intervertebral disc cavity.

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Ducheyne et al.), U.S. Pat. No. 5,122,154 (Rhodes),.U.S. Pat. No. 5,204,106 (Schepers at al.), U.S. Pat. No. 5,888,220 (Felt et al.) and U.S. Pat. No. 5,376,120 (Sarver et al.).

It should be understood that the examples and embodiments described herein are for illustrative purposes only and that various modifications or changes in light thereof will be suggested to persons skilled in the art and are to be included within the spirit and preview of this application and the scope of the appended claims.

The invention claimed is:

1. A method for repairing an intervertebral disc, wherein said intervertebral disc comprises a disc nucleus and a disc annulus, comprising the steps of:
   a) forming an aperture in said intervertebral disc annulus; and
   b) securing across said aperture to said intervertebral disc annulus an annulus stent comprising:
      a centralized vertical extension with an upper section and a lower section, and
      a recess in the lower section enabling the annulus stent to form a compatible fit with the edges of an aperture,
         the upper section of the centralized vertical extension comprising at least one orifice through the upper section, the at least one orifice being sized and shaped to accommodate a suture, tension band, or staple, and
         the suture, tension band, or staple configured to pass into or through tissues surrounding the aperture of the intervertebral disc.

2. The method for repairing an intervertebral disc according to claim 1, wherein at least a portion of said annulus stent is formed at least in part of human muscle fascia, an autograft, an allograft, or a xenograft.

3. The method for repairing an intervertebral disc according to claim 1, further comprising the step of preparing said intervertebral disc, wherein said preparation step comprises the steps:
   i. identifying a damaged section of said disc nucleus; and
   ii. removing said damaged section of said disc nucleus.

4. A method for repairing an intervertebral disc, wherein said intervertebral disc comprises a disc nucleus and a disc annulus, comprising the steps of:
   i. forming an aperture in said intervertebral disc annulus;
   ii. inserting an annulus stent into said aperture, wherein said annulus stent comprises a central portion with an upper section and a lower section, and
      a recess in the lower section enabling the annulus stent to form a compatible fit with the edges of the aperture,
         the upper section of the central portion comprising at least one orifice through the upper section, the at least one orifice being sized and shaped to accommodate a suture, tension band, or staple, and
         the suture, tension band, or staple configured to pass into or through tissues surrounding the aperture of the intervertebral disc, and
         the lower section comprising a left lateral extension and a right lateral extension; and
   iii. securing said annulus stent to said intervertebral disc annulus.

5. The method for repairing an intervertebral disc according to claim 4, wherein said step of forming said aperture in said disc annulus comprises the step of making a surgical incision into said disc annulus.

6. The method for repairing an intervertebral disc according to claim 4, wherein said step of inserting said annulus stent into said aperture comprises the steps of:
   a) compressing said left and right lateral extensions together;
   b) inserting said annulus stent into said aperture, such that an upper surface of said left and right lateral extensions conforms to an inside surface of said disc annulus; and
   c) positioning said central portion within said aperture, such that said annulus stent may be secured to said disc annulus.

7. The method for repairing an intervertebral disc according to claim 4, wherein said step of inserting said annulus stent into said aperture comprises the steps of:
   a) compressing said left and right lateral extension together;
   b) rotating said annulus stent, such that said annulus stent may be laterally inserted into said intervertebral disc;
   c) inserting said annulus stent laterally through said aperture into said intervertebral disc;
   d) rotating said annulus stent within said intervertebral disc, such that an upper surface of said left and right lateral extensions conforms to an inside surface of said disc annulus; and
   e) positioning said central portion within said aperture, such that said annulus stent may be secured to said disc annulus.

8. The method for repairing an intervertebral disc according to claim 4, further comprising a step of preparing said intervertebral disc, wherein said preparation step comprises the steps of inserting a first surgical screws into a vertebra adjacent said intervertebral disc and a second surgical screws into an opposing vertebra, wherein said surgical screw comprises an eye hole located at the top of said surgical screw.

9. The method for repairing an intervertebral disc according to claim 8, wherein said step of securing said annulus stent to said intervertebral disc comprises the steps of threading a surgical suture through said eye hole on said surgical screw.

10. The method for repairing an intervertebral disc according to claim 4, further comprising the step of preparing said intervertebral disc, wherein said preparation step comprises the steps:
   a) identifying a damaged section of said disc nucleus; and
   b) removing said damaged section of said disc nucleus.

11. The method for repairing an intervertebral disc according to claim 10, wherein said annulus stent comprises a bladder having an inner cavity, the bladder attached to a lower surface of said lower section and said step of inserting said annulus stent into said aperture comprises the steps of:
   a) compressing said left and right lateral extensions together;
   b) inserting said annulus stent into said aperture, such that an upper surface of said left and right lateral extensions conforms to an inside surface of said disc annulus;
   c) positioning said central portion within said aperture, such that said annulus stent may be secured to disc annulus; and
   d) injecting a biocompatible fluid into said internal cavity, through said annulus stent.

12. The method for repairing an intervertebral disc according to claim 11, wherein said biocompatible fluid comprises a hygroscopic material.

13. The method for repairing an intervertebral disc according to claim 10, wherein said annulus stent comprises a bladder having an inner cavity, the bladder attached to a lower surface of said lower section and said step of inserting said annulus stent into said aperture comprises the steps of:
   a) compressing said left and right lateral extensions together;
   b) rotating said annulus stent, such that said annulus stent may be laterally inserted into said intervertebral disc;
   c) inserting said annulus stent laterally through said aperture into said intervertebral disc;
   d) rotating said annulus stent within said intervertebral disc, such that an upper surface of said lower section conforms to an inside surface of said disc annulus;
   e) positioning said central portion within said aperture, such that said annulus stent may be secured to disc annulus; and
   f) injecting a biocompatible fluid into said internal cavity, through said annulus stent.

14. The method for repairing an intervertebral disc according to claim 13, wherein said biocompatible fluid comprises a hygroscopic material.

* * * * *